United States Patent
Reker-Hadrup et al.

(10) Patent No.: US 9,151,757 B2
(45) Date of Patent: Oct. 6, 2015

(54) DETECTING ANTIGEN RESPONSIVE CELLS IN A SAMPLE

(75) Inventors: Sine Reker-Hadrup, Virum (DK); Arnold Hendrik Bakker, Berkeley, CA (US); Cheng Yi Jenny Shu, Boston, MA (US); Antonius Nicolaas Maria Schumacher, Haarlem (NL)

(73) Assignees: Stichting Sanquin Bloedvoorziening, Amsterdam (NL); Stichting het Nederlands Kanker Instituut, Amsterdam (NL)

( * ) Notice: Subject to any disclaimer, the term of this patent is extended or adjusted under 35 U.S.C. 154(b) by 1135 days.

(21) Appl. No.: 13/127,136

(22) PCT Filed: Nov. 3, 2008

(86) PCT No.: PCT/EP2008/009356
§ 371 (c)(1),
(2), (4) Date: Jun. 24, 2011

(87) PCT Pub. No.: WO2010/060439
PCT Pub. Date: Jun. 3, 2010

(65) Prior Publication Data
US 2011/0269155 A1 Nov. 3, 2011

(51) Int. Cl.
*G01N 33/58* (2006.01)
*G01N 33/569* (2006.01)

(52) U.S. Cl.
CPC .......... *G01N 33/56972* (2013.01); *G01N 33/58* (2013.01)

(58) Field of Classification Search
CPC .................. G01N 33/56972; G01N 33/58
See application file for complete search history.

(56) References Cited

PUBLICATIONS

Bakker et al. Conditional MHC class I ligands and peptide exchange technology for the human MHC gene products HLA-A1, -A3, -A11 and -B7, PNAS 105 (10): 3825-3830 (Mar. 2008).*
Bakker et al. MHC multimer technology: current status and future prospects, Current Opinion in Immunology GB, 17 (4), 2005-2008 (Aug. 2005).*
Chattopadhyay et al. Quantum dot semiconductor nanocrystals for immunophenotyping by polychromatic flow cytometry, Nature Medicine 12 (8) 972-977 (Aug. 2006).*
Toebes et al., "Design and use of conditional MHC class I ligands", Nature Medicine, Feb. 2006, pp. 246-251, vol. 12, No. 2.
Rodenko et al., "Generation of peptide-MHC class I complexes through UV-mediated ligand exchange", Nature Protocols, Aug. 31, 2006, pp. 1120-1132, vol. 1, No. 3.
(Continued)

*Primary Examiner* — Gail R Gabel
(74) *Attorney, Agent, or Firm* — The Webb Law Firm

(57) ABSTRACT

The present invention relates to methods for detecting antigen responsive cells in a sample using multidimensional labeled antigen presenting compounds, such as antigen-major histocompatibility complexes (NHC). Further, the present invention relates to the use of the present multidimensional labeled antigen presenting compounds, such as antigen-major histocompatibility complexes (MHC), for detecting antigen responsive cells in a sample, preferably a single sample, such as a blood sample. The present method allows high-throughput analysis of specific antigen responsive cells, such as T- and B-cells, thereby providing, for example, high-throughput methods for monitoring of diseases or conditions and the development of immunotherapeutics, vaccines, or the identification epitopes or immunogenic amino acid sequences.

17 Claims, 11 Drawing Sheets

(56) References Cited

PUBLICATIONS

Arstila et al., "A direct estimate of the human αβ T cell receptor diversity", Science, Oct. 29, 1999, pp. 958-961, vol. 286.

Bakker et al., Conditional MHC class I ligands and peptide exchange technology for the human MHC gene products HLA-A1, -A3, -A11, and -B7, PNAS, Mar. 11, 2008, pp. 3825-3830, vol. 105, No. 10.

Bakker et al., MHC multimer technology: current status and future prospects, Current Opinion in Immunology, 2005, pp. 428-433, vol. 17.

Chattopadhyay et al., "Quantum dot semiconductor nanocrystals for immunophenotyping by polychromatic flow cytometry," Nature Medicine, Aug. 2006, pp. 972-977, vol. 12, No. 8.

Xu et al., "Multiplexed SNP genotyping using the QbeadTM system: a quantum dot-encoded microsphere-based assay," Nucleic Acids Research, 2003, pp. 1-10, vol. 31, No. 8 e43.

Hadrup et al., "Parallel detection of antigen-specific T-cell responses by multidimensional encoding of MHC multimers," Nature Methods, Jul. 2009, pp. 520-526, plus 2 sheets, vol. 6, No. 7.

Altman et al., "Phenotypic Analysis of Antigen-Specific T Lymphocytes," Science, Oct. 4, 1996, pp. 94-96, vol. 274, No. 5284.

Soen et al., "Detection and Characterization of Cellular Immune Responses Using Peptide-MHC Microarrays," PLoS Biology, Dec. 22, 2003, pp. 429-438, vol. 1, Issue 3.

Stone et al., "HLA-restricted epitope identification and detection of functional T cell responses by using MHC-peptide and costimulatory microarrays," PNAS, Mar. 8, 2005, pp. 3744-3749, vol. 102, No. 10.

Haanen et al., "Selective Expansion of Cross-reactive CD8+ Memory T Cells by Viral Variants," J. Exp. Med., Nov. 1, 1999, pp. 1319-1328, vol. 190, No. 9.

Van Oijen et al., "On the Role of Melanoma-Specific CD8+ T-Cell Immunity in Disease Progression of Advanced-Stage Melanoma Patients," Clinical Cancer Research, Jul. 15, 2004, pp. 4754-4760, vol. 10.

Garboczi et al., "HLA-A2-peptide complexes: Refolding and crystallization of molecules expressed in *Escherichia coli* and complexed with single antigenic peptides," Proc. Natl. Acad. Sci. USA, Apr. 1992, pp. 3429-3433, vol. 89.

\* cited by examiner

|  | PE | APC | QD565 | QD585 | QD605 | QD655 | QD705 | QD800 |
|---|---|---|---|---|---|---|---|---|
| PE | x | x | x | x | x | x | x | x |
| APC |  | x | x | x | x | x | x | x |
| QD565 |  |  | x | x | x | x | x | x |
| QD585 |  |  |  | x | x | x | x | x |
| QD605 |  |  |  |  | x | x | x | x |
| QD655 |  |  |  |  |  | x | x | x |
| QD705 |  |  |  |  |  |  | x | x |
| QD800 |  |  |  |  |  |  |  | x |

Figure 2

SEQUENCE LISTING

<160> NUMBER OF SEQ ID NOS: 25

<210> SEQ ID NO 1
<211> LENGTH: 10
<212> TYPE: PRT
<213> ORGANISM: Homo sapiens

<400> SEQUENCE: 1

Gln Leu Arg Ala Leu Asp Gly Gly Asn Lys
1               5                   10

<210> SEQ ID NO 2
<211> LENGTH: 9
<212> TYPE: PRT
<213> ORGANISM: Homo sapiens

<400> SEQUENCE: 2

Ser Leu Tyr Arg Asp Pro Leu Pro Arg
1               5

<210> SEQ ID NO 3
<211> LENGTH: 9
<212> TYPE: PRT
<213> ORGANISM: Homo sapiens

<400> SEQUENCE: 3

His Ala Tyr Ile Gln Ser Leu Leu Lys
1               5

<210> SEQ ID NO 4
<211> LENGTH: 9
<212> TYPE: PRT
<213> ORGANISM: Homo sapiens

<400> SEQUENCE: 4

Arg Met Tyr Asn Met Val Pro Phe Phe
1               5

<210> SEQ ID NO 5
<211> LENGTH: 9
<212> TYPE: PRT
<213> ORGANISM: Homo sapiens

<400> SEQUENCE: 5

Gly Thr Tyr Glu Gly Leu Leu Arg Arg
1               5

<210> SEQ ID NO 6
<211> LENGTH: 10
<212> TYPE: PRT
<213> ORGANISM: Homo sapiens

<400> SEQUENCE: 6

Ile Ala Leu Asn Phe Pro Gly Ser Gln Lys
1               5                   10

<210> SEQ ID NO 7
<211> LENGTH: 9
<212> TYPE: PRT
<213> ORGANISM: Homo sapiens

<400> SEQUENCE: 7

Leu Ile Tyr Arg Arg Arg Leu Met Lys
1               5

<210> SEQ ID NO 8
<211> LENGTH: 9
<212> TYPE: PRT
<213> ORGANISM: Homo sapiens

<400> SEQUENCE: 8

Gly Thr Ala Thr Leu Arg Leu Val Lys

```
1               5

<210> SEQ ID NO 9
<211> LENGTH: 9
<212> TYPE: PRT
<213> ORGANISM: Homo sapiens

<400> SEQUENCE: 9

Ala Leu Leu Ala Val Gly Ala Thr Lys
1               5

<210> SEQ ID NO 10
<211> LENGTH: 9
<212> TYPE: PRT
<213> ORGANISM: Homo sapiens

<400> SEQUENCE: 10

Ala Leu Asn Phe Pro Gly Ser Gln Lys
1               5

<210> SEQ ID NO 11
<211> LENGTH: 9
<212> TYPE: PRT
<213> ORGANISM: Homo sapiens

<400> SEQUENCE: 11

Gly Val Ser Arg Gln Leu Arg Thr Lys
1               5

<210> SEQ ID NO 12
<211> LENGTH: 9
<212> TYPE: PRT
<213> ORGANISM: Homo sapiens

<400> SEQUENCE: 12

Gln Leu Val Leu His Gln Ile Leu Lys
1               5

<210> SEQ ID NO 13
<211> LENGTH: 9
<212> TYPE: PRT
<213> ORGANISM: Homo sapiens

<400> SEQUENCE: 13

Lys Thr Lys Pro Leu Ser Met Leu Tyr
1               5

<210> SEQ ID NO 14
<211> LENGTH: 9
<212> TYPE: PRT
<213> ORGANISM: Homo sapiens

<400> SEQUENCE: 14

Arg Val Ala Gly Glu Cys Trp Pro Arg
1               5

<210> SEQ ID NO 15
<211> LENGTH: 10
<212> TYPE: PRT
<213> ORGANISM: Homo sapiens

<400> SEQUENCE: 15

Tyr Met Val Pro Phe Ile Pro Leu Tyr Arg
1               5                   10
```

<210> SEQ ID NO 16
<211> LENGTH: 9
<212> TYPE: PRT
<213> ORGANISM: Homo sapiens

<400> SEQUENCE: 16

Ser Leu Leu Cys Arg His Lys Arg Lys
1               5

<210> SEQ ID NO 17
<211> LENGTH: 9
<212> TYPE: PRT
<213> ORGANISM: Homo sapiens

<400> SEQUENCE: 17

Val Ser Ser Lys Asn Leu Met Glu Lys
1               5

<210> SEQ ID NO 18
<211> LENGTH: 10
<212> TYPE: PRT
<213> ORGANISM: Homo sapiens

<400> SEQUENCE: 18

Gly Leu Val Ser Leu Leu Cys Arg His Lys
1               5                   10

<210> SEQ ID NO 19
<211> LENGTH: 10
<212> TYPE: PRT
<213> ORGANISM: Homo sapiens

<400> SEQUENCE: 19

Ser Leu Pro Tyr Trp Asn Phe Ala Thr Arg
1               5                   10

<210> SEQ ID NO 20
<211> LENGTH: 9
<212> TYPE: PRT
<213> ORGANISM: Homo sapiens

<400> SEQUENCE: 20

Ala Ser Tyr Leu Ile Arg Ala Arg Arg
1               5

<210> SEQ ID NO 21
<211> LENGTH: 10
<212> TYPE: PRT
<213> ORGANISM: Homo sapiens

<400> SEQUENCE: 21

Thr Leu Leu Gly Pro Gly Arg Pro Tyr Arg
1               5                   10

<210> SEQ ID NO 22
<211> LENGTH: 9
<212> TYPE: PRT
<213> ORGANISM: Homo sapiens

<400> SEQUENCE: 22

Val Leu Leu Ala Phe Leu Gln Tyr Arg
1               5

<210> SEQ ID NO 23

```
<211> LENGTH: 9
<212> TYPE: PRT
<213> ORGANISM: Homo sapiens

<400> SEQUENCE: 23

Ile Leu Arg Gly Ser Val Ala His Lys
1               5

<210> SEQ ID NO 24
<211> LENGTH: 9
<212> TYPE: PRT
<213> ORGANISM: Homo sapiens

<400> SEQUENCE: 24

Arg Leu Arg Ala Glu Ala Gln Val Lys
1               5

<210> SEQ ID NO 25
<211> LENGTH: 9
<212> TYPE: PRT
<213> ORGANISM: Homo sapiens

<400> SEQUENCE: 25

Arg Val Arg Ala Tyr Thr Tyr Ser Lys
1               5
```

DETECTING ANTIGEN RESPONSIVE CELLS IN A SAMPLE

The Sequence Listing associated with this application is filed in electronic format via EFS-Web and is hereby incorporated by reference into the specification in its entirety. The name of the text file containing the Sequence Listing is 111612_ST25.txt. The size of the text file is 8,192 bytes, and the text file was created on Jan. 2, 2014.

The present invention relates to methods for detecting antigen responsive cells in a sample using multidimensional labeled antigen presenting compounds, such as major histocompatibility complexes (MHC). Further, the present invention relates to the use of the present multidimensional labeled antigen presenting compounds, such as antigen-major histocompatibility complexes (MHC), for detecting antigen responsive cells in a sample, preferably a single sample, such as a blood sample. The present method allows high-throughput analysis of specific antigen responsive cells, such as T- and B-cells, thereby providing, for example, high-throughput methods for monitoring of diseases or conditions and the development of immunotherapeutics, vaccines, or the identification epitopes or immunogenic amino acid sequences.

Antigen responsive cells, such as T-cells and B-cells, are capable of, amongst others, recognizing virus-infected cells and tumor cells by monitoring the presence of disease-specific peptide-major histocompatibility complexes (MHC) using their clone-specific T cell receptor (TCR). The repertoire of different TCRs expressed on the combined pool of human T cells is vast and estimated to be around 25 million (Arstila et al., 1999).

For monitoring diseases or conditions and the development of immunotherapeutics or vaccines, it is essential to be able to detect, identify, or isolate, only those specific antigen responsive cells, such as T cells and B-cells, that recognize, though, for example, the clone-specific T cell receptor (TCR), a specific antigen-MHC (aMHC) complex, such as a peptide-MHC (pMHC) complex, within a large pool of irrelevant antigen responsive cells, i.e., cells not comprising the antigen specific receptor.

As first shown by Altman et al., 1996, soluble multimeric pMHC complexes coupled to fluorochromes can be used to detect antigen-specific T cells by flow cytometry. The use of these fluorescent MHC multimers has become a cornerstone of T cell monitoring both in research and in clinical monitoring.

However, a major limitation in the use of MHC multimer flow cytometry for detection of antigen-specific T cell responses is formed by the fact that only a few antigen specificities (and often only a single) can be monitored for a single biological sample. This limitation is due to the restricted number of "channels", i.e., different labels such as fluorochromes, that can be distinguished by either their excitation or emission spectra or that can be detected by flow cytometry, and this forms a severe limit on the number of T cell responses that can be analyzed within the restricted amount of biological material, such as a single peripheral blood sample, that is generally available.

Biological materials are for instance analyzed to monitor naturally occurring immune responses, such as those that can occur upon infection or cancer. In addition, biological materials are analyzed for the effect of immunotherapeutics including vaccines on immune responses. Immunotherapeutics as used herein are defined as active components in medical interventions that aim to enhance or suppress immune responses, including vaccines, non-specific immune stimulants, immunesuppressives, cell-based immunotherapeutics and combinations thereof.

Even with the recent development quantum dots (Qdots) as new inorganic fluorochromes, and the steady increase in multi-parameter detection possibilities of flow cytometry apparatuses, the maximum number of different T cell populations analyzed in a single sample by pMHC multimer staining remains at four (Chattopadhyay et al., 2006).

The requirement for the development of technologies that allow a more comprehensive analysis of antigen-specific T cell responses is underscored by the fact that several groups have tried to develop so-called MHC microarrays. In these systems, T cell specificity is not encoded by fluorochromes, but is spatially encoded (Soen et al., 2003; and Stone et al., 2005). In spite of their promise, MHC microarrays have not become widely adopted, and no documented examples for its value in the multiplexed measurement of T cell responses, for instance epitope identification, are available.

Combinatorial coding systems have been used in a number of settings to increase the number of analyses that can be performed on a single sample. A specific example in the field of Qdots is formed by the use of Qdot-coded microbeads to perform genotyping (Xu et al., 2003). In addition, combinatorial coding has been used to measure serum products such as cytokines using bead arrays in which encoding is performed by variation in bead size, fluorochrome and fluorochrome intensity (e.g. the BD cytometric bead arrays). In all these examples, solutes are analyzed by binding to pre-encoded microbeads.

Considering the above, there remains a need in the art for methods allowing detection, isolation and/or identification of specific antigen responsive cells, such as antigen specific T-cells, in a high-throughput manner.

Further, there remains a need in the art, considering the often limited amounts of sample available, for methods allowing detection, isolation and/or identification of multiple species of specific antigen responsive cells, such as T-cells, in a single sample.

SUMMARY OF THE INVENTION

Therefore, it is an objective of the present invention, amongst others, to provide methods for detecting multiple species of antigen specific cells in relatively small amounts of biological material, such as in a single sample, for example, a single peripheral blood sample, preferably in a high-throughput manner.

This objective, amongst others, is met by a method as defined in the appended claim 1.

Specifically, this objective is met by a method for detecting antigen responsive cells in a sample (of biological material such as a peripheral blood sample) comprising:
 providing, such as loading, antigen presenting compounds, carrying at least one label, with two or more predetermined antigens, wherein each antigen is represented (encoded) by at least two different labels;
 contacting said antigen-provided antigen presenting compounds with said sample;
 detecting binding of said antigen loaded antigen presenting compounds to said antigen responsive cells, thereby detecting cells responsive to said antigen;
wherein said antigen is detected by detecting the presence of said at least two different labels bound to an antigen responsive cell through said antigen presenting compounds loaded with said antigen.

According to an preferred embodiment of the present invention, the above two or more predetermined antigens are selected from the group consisting of three or more, four or more, five or more, six or more, seven or more, eight or more, ten or more, eleven or more, twelve or more, thirteen or more, fourteen or more, fifteen or more, sixteen or more, seventeen or more, eighteen or more, nineteen or more, twenty or more, twenty or more, twenty-one or more, twenty-two or more, twenty-three or more, twenty-four or more, twenty-five or more, twenty-six or more, twenty-seven or more, and twenty-eight or more.

The present invention extends the concept of combinatorial coding by the analysis of combinatorial codes that are formed through the binding of defined combinations of antigen presenting compounds.

Specifically, the present invention is based on the discovery that a large number of antigen specific cell responses can be analyzed simultaneously, and in a single sample, through the use of antigen presenting compounds that are each coupled to a unique combination of labels, such as fluorochromes, with the same label being used many times, but each time in a unique combination with one or more other labels, such as fluorochromes.

In contrast with the prior art, this involves the de novo creation of a code specific for the assay; this involves an analysis on cells rather than solutes; and this involves the use of combinatorial coding for the parallel analysis of antigen-specific cell responses.

The data obtained show that, in spite of the widely held view that antigen-specific cells are highly cross-reactive, detection of cells by combinatorial coding is a practical and realistic possibility. The value of combinatorial coding is exemplified according to the present invention by the dissection of melanoma-associated antigen-specific T cell responses in peripheral blood from melanoma patients.

Prior work has shown that is feasible to detect antigen-specific T cells by binding of two MHC multimers containing the same, or a related peptide, thus the detection of a single antigen in a single sample, that are both coupled to a different fluorochrome. This technology of double MHC multimer staining was used to reveal the fine specificity of T cells specific for (variants of) single peptide epitopes (Haanen et al., 1999).

According to the present invention, the term "antigen" indicates an immunogenic peptide or polypeptide which as recognized by the immune system as "foreign" or heterologous.

The present inventor contemplated that if a large set of such dual-color encoded pMHCs could be combined within a single sample without interfering with the ability to detect T cells specific for one of these pMHCs, such a technology could conceivably be utilized to encode a much larger number of T cell specificities than possible with classical single color encoding.

In this setting, a specific T cell population would no longer be defined by a single fluorescent signal, as is the case in the prior art pMHC multimer stainings, but its clonal specificity is visualized by binding of two predetermined fluorochromes and not any of the other fluorochromes, alone or in combination, that are present. The power of such a combinatorial encoding scheme becomes increasingly apparent with an increasing number of available fluorochromes.

As an example, in a setting where 3 fluorochromes can be used to encode, a single and dual coding system can both be used to reveal three different identities ('A', 'B', and 'C' in case of single color encoding and 'A-B', 'A-C', and 'B-C' in case of two color encoding); In case 8 fluorochromes would be used to encode, a single and dual coding system may deliver 8 and 28 unique codes, respectively; In case 17 fluorochromes are used (the maximal number of different fluorochromes presently available for a single flow cytometric analysis), a single coding system would yield 17 unique codes whereas a dual coding system could encompass up to 136 different identities.

Although the present invention exemplifies 2-dimensional combinatorial coding, thus two fluorochromes for coding a single antigen, three or higher order, such as four and five, combinatorial coding works by the same principle and is particularly attractive with increasing numbers of available fluorochromes. To illustrate this, in the latter example in which 17 fluorochromes are utilized, higher order encoding schemes allow the encoding of many thousands of unique specificities.

One of the key factors determining whether the above combinatorial encoding would be available in a single sample is the ability to measure antigen-responsive cells by interaction with multiple labels in a case where labels are used multiple times and conjugated to multiple distinct antigen-antigen presenting compounds. The use of the same label conjugated to distinct antigen-antigen presenting compounds inherently raises the possibility that antigen-responsive cells may be labeled by distinct antigen-antigen presenting compounds, thereby destroying the possibility to reveal its antigen-responsiveness by codes such as provided in Table 1 below.

Contrary to the widely held view that T cells are highly cross-reactive, the present inventors have surprisingly discovered that the multiple use of the same label conjugated to distinct antigen-antigen presenting compounds does allow the detection of antigen-responsive cells:

Another one of the key factors determining whether the above combinatorial encoding would be available in a single sample is the discriminative power of the method, or, in other words, the ability to separately detect each individual combination of labels, such as fluorochromes. The use of a label such as a fluorochrome inherently provides a background signal below which no specific detection is possible. From this, it inherently follows that the background signal would increase, thus the detection limit, when using two labels, and further increases when using three labels, etc.

The present inventors have surprisingly discovered that, in contrast with the expected decrease in discriminative power due to an increase in background (aspecific) signal, the encoding of multiple antigens using two or more labels, such as fluorochromes, decreases the background signal with a factor of as much as 10 in a 2 label antigen coding system, thereby allowing a substantial increase in sensitivity of the system. Due to this increased sensitivity of the system, multiple detections of antigens, i.e., the detection of multiple species antigen responsive cells, has become a possibility, thereby providing the method according to the present invention.

Further, amongst others due to the above observed decrease in background signal, thus an increased sensitivity, the expected negative influence on the sensitivity of the assay due to antigen presenting compound aspecific binding is significantly reduced, thereby further providing the method according to the present invention.

According to a preferred embodiment of the present method, the antigen presenting compounds are provided with one label and the antigen is represented, or encoded, by at least two differently labelled antigen presenting compounds.

In other words, according to this preferred embodiment, each individual antigen (or epitope) to be detected is loaded on at least two antigen presenting compounds each having a differently detectable label, such as different fluorescence emitting fluorochromes.

According to another preferred embodiment of the present method, the antigen presenting compounds are provided with at least two different labels, such as two, three, four, five, six, seven or eight, for example conjugated or covalently bound to the MHCs, and the antigen is represented (or encoded) by one multiple-labelled antigen presenting compound.

In other words, according to this preferred embodiment, each individual antigen (or epitope) to be detected is loaded on a single antigen presenting compound provided with at least two different labels, such as different fluorescence emitting fluorochromes.

The antigen according to the present invention is preferably a peptide. This peptide can represent an already known immunogenic epitope of, for example a virus or a tumour cell, thereby allowing, for example, detection of the presence immune cells responsive to this antigen and the subsequent diagnosis of a viral infection or cancer.

The present peptide can also represent an unknown epitope and the detection of cells responsive to this epitope is indicative for the presence of an immunogenic amino acid sequence within this peptide thereby allowing the identification of immunogenic regions or epitopes in, for example, a polypeptide.

Antigen presenting compounds according to the present invention preferably link the antigen to the attached label or labels. In case of T cells, the antigen presenting compounds according to the present invention are preferably major histocompatibility complexes (MHC) and, more preferably, multimeric major histocompatibility complexes (MHC), preferably four or more. In case of T cells, but not for instance in case of B cells, the antigen-presenting compounds will preferably contribute energetically to, thus increase, the interaction between antigen and antigen-responsive cell.

The use of major histocompatibility complexes (MHC) is advantageous, not only because these compounds are naturally capable of antigen presentation, but also because readily available technologies are available to provide the present labelled antigen presenting compounds for use in the present method (Rodenko et al., 2006).

The preferred antigen responsive cells according to the present invention are T-cells and/or B-cells, more preferably T-cells.

The labels according to the present invention are preferably fluorescent labels, more preferably fluorescent labels designated as in the art as Qdots.

According to a preferred embodiment of the present method, the number of different labels used in a single assay is selected from the group consisting three or more, four or more, five or more, six or more, seven or more, and eight or more.

According to yet another preferred embodiment, each individual antigen is represented by at least three or at least four different labels. By using tree or more, or even four or more, labels, such as Qdots, to encode a single antigen, the number of potential antigen responsive cells to be detected in a single dramatically increases. This is exemplified in FIG. 1, showing the number of available channels, or combinations, available to encode, or represent a single antigen.

While a single label encoding a single antigen would allow the discrimination of as many species of antigen responsive cells as the number of available labels, encoding the same antigen by two, three, or four labels dramatically increases the number species of antigen representing cells that can be detected.

According to the present invention, the present method is preferably performed in a single sample, wherein the sample is preferably a blood sample.

As defined herein, the term "blood samples" is not limited to blood samples directly obtained from an individual, but also to samples derived, or originating from, a directly obtained blood sample, under the restriction that these derived samples still comprise the antigen responsive cells originally present.

According to a particularly preferred embodiment of the present method, the detection of antigen responsive cells comprises flow cytometry analysis.

Considering the above, the present invention also relates, other to another aspect, to the use of the present at least two labels representing a single antigen for the detection of antigen responsive cells in a sample.

According to a further aspect, the present invention relates to the use of the present method for diagnosing diseases or conditions such as cancer.

According to yet a further aspect, the present invention relates to the use of the present method for developing immunotherapeutics.

According to another aspect, the present invention relates to the use of the present method for vaccine development.

According to still another aspect, the present invention relates to the use of the present method for the identification of epitopes, or immunogenic amino acid sequences, in a polypeptide. This aspect is exemplified in the below described identification of the unknown HLA-A3 associated T cells antigens: QLRALDGGNK (SEQ ID NO: 1), SLYRDPLPR (SEQ ID NO: 2), HAYIQSLLK (SEQ ID NO: 3), RMYNMVPFF (SEQ ID NO: 4) and GTYEGLLRR (SEQ ID NO: 5) using the method according to the present invention.

Accordingly, the present invention also relates to HLA-A3 associated T cells antigens selected from the group consisting of QLRALDGGNK (SEQ ID NO: 1), SLYRDPLPR (SEQ ID NO: 2), HAYIQSLLK (SEQ ID NO: 3), RMYNMVPFF (SEQ ID NO: 4) and GTYEGLLRR (SEQ ID NO: 5); the use of the present HLA-A3 associated T cells antigens, or functional derivatives thereof, in the monitoring of immunotherapeutics and vaccines; and the use of the present HLA-A3 associated T cells antigens, or functional derivatives thereof, in the development of immunotherapeutics and vaccines.

BRIEF DESCRIPTION OF THE DRAWINGS

The principles of the present invention will be further detailed in the examples showing preferred embodiments of the present invention. In the examples, reference is made to the following figures wherein:

FIG. 2: shows the 28 unique color combinations that can be used to encode an antigen using a 2-dimensional matrix of 8 fluorochromes

EXAMPLES

Methods

Generation of Peptide-MHC Complexes

Figure 1:
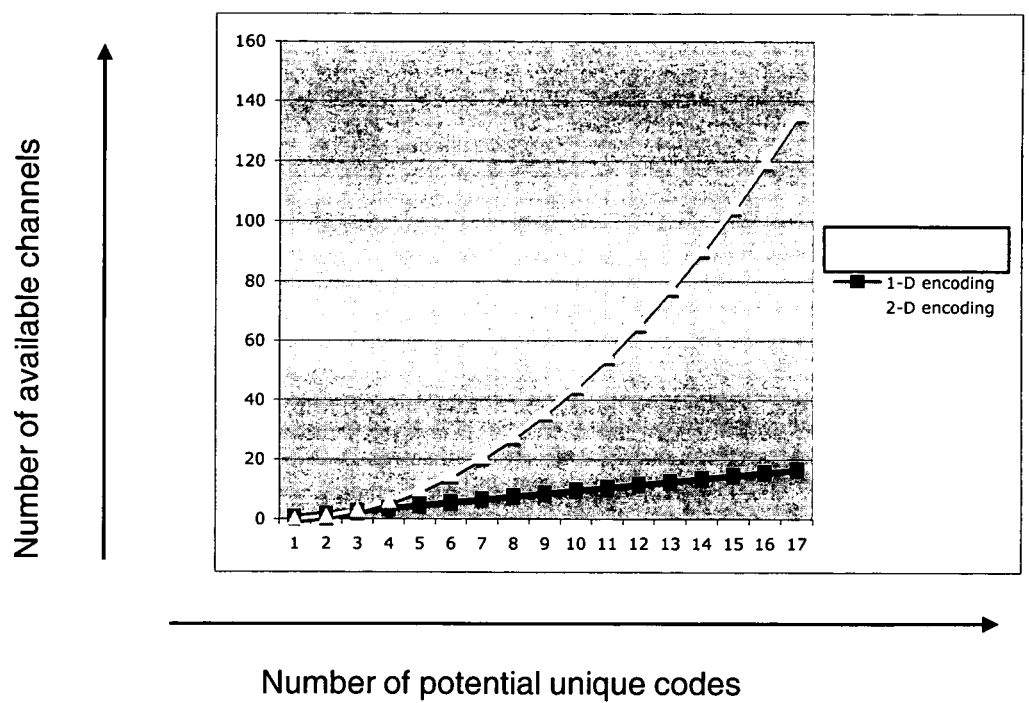
FIG. 1: shows the theoretical number of unique color combinations that can be made using an increasing number of fluorochromes in either 1- and 2-dimensional (left) or 1-4-dimensional (right) coding schemes.

All peptides were synthesized in-house using standard Fmoc chemistry or purchased from Pepscan (Pepscan Presto BV, Lelystad, NL). The UV-sensitive building block J was synthesized as described (Toebes et al., 2006). Recombinant HLA-A1, -A2, -A3 and -B7 heavy chains and human β₂m light chain were produced in *Escherichia coli*. MHC class I refolding reaction were performed as described (Garboczi et al., 1992) and MHC class I complexes were purified by gel-filtration HPLC in PBS (pH 7.4).

Specific peptide-HLA complexes were generated by MHC peptide exchange. p*HLA complexes (100 μg/mL) were subjected to 366 nm UV light (Camag) for one hour in presence of the indicated peptide (200 μM). After exchange, samples were spun at 16,000 g for 5 min, and supernatants were used for MHC multimer formation.

Generation of MHC Multimers

MHC multimers were generated using 8 different fluorescence-streptavidin (SA) conjugates (Invitrogen): SA-Qdot565, SA-Qdot585, SA-Qdot605, SA-Qdot655, SA-Qdot705, SA-Qdot800, SA-phycoerectin (PE) and SA-allophycocyanin (APC). For each 100 μL of MHC monomer (conc. 100 μg/mL) 7.08 μL SA-Qdot conjugate (1 μM), 10.8 μL SA-PE (1 mg/ml), or 6 μL SA-APC (1 mg/ml) was added, followed by incubation on ice for 20 min. Assuming a 100% rescue after MHC peptide exchange, this would result in an occupancy of 30 MHC monomers per SA-Qdot. Biotin (Sigma) and NaN₃ (Sigma) were added to a final concentration of 26.4 μM and 0.02%, respectively, followed by incubation on ice for 20 min. PE and APC labeled complexes were diluted 2-fold in PBS with 0.02% NaN₃. For each pMHC complex, multimers were made with two different fluorescent labels according to the schemes in Table 1 and Table 2.

For combinatorial T cell stainings, multimer complexes of the same specificity were mixed 1:1 for Q605, Q655, Q705, PE and APC labeled complexes and 2:1 for Q565, Q585 and Q800 labeled complexes in combination with any other color. Combinations of Q565, Q585 and Q800 were excluded. Combined pMHC mixtures for analysis of T cell responses by combinatorial coding were generated by pooling and were stored at 4° C. as a 50-fold concentrated ready-to-use stocks for T cell staining. Before use, MHC multimers were spun at 17,000 g for 2 min and supernatant was used.

T Cell Staining

For T cell staining of approx. $1 \times 10^6$ PBMCs or $2 \times 10^5$ cultured T cells, 2 µL of single pMHC multimer, or 50 µL of dual color-encoded pMHC collections (final concentration: 2 µg/mL per distinct pMHC based on initial monomer concentration) was used. Final staining volume was 80 µl and cells were incubated for 10 min at 37° C. Next, 20 µL of a 5 times antibody-mix consisting of CD8-Alexa700 (Caltech MHCD0289) (final dilution 1/200), CD4-FITC (BD 345768) (final dilution 1/8), CD14-FITC (BD 345784) (final dilution 1/32), CD19-FITC (BD345776) (final dilution 1/16), CD40-FITC (Serotech MCA1590F) (final dilution 1/40), CD16-FITC (BD 347523) (final dilution 1/64) was added and cells were incubated for 20-30 min at 4° C. Prior to flow cytometry, cells were washed twice and Propidium Iodide was added to allow dead cell exclusion.

Flow Cytometry

Data acquisition was performed on an LSR-II flow cytometer (Becton Dickinson) with FacsDiva software using the following 11-color instrument settings: 488 nm laser: PI: 685LP, 695/40; PE: 550LP, 575/26; FITC: 505LP, 530/30; SSC: 488/10. 633 nm laser: Alexa700: 685LP, 730/45; APC: 660/20. 405 nm laser: Qdot800: 770LP, 800/30; Qdot705: 680LP, 710/50; Qdot655: 635LP, 660/40; Qdot605: 595LP, 650/12. 355 nm laser: Qdot585: 575LP, 585/15; Qdot565: 545LP: 560/20.

Approximately 200,000 lymphocytes were recorded for each analysis. To identify antigen specific T cells the following gating strategy was used: 1). Selection of live single-cell lymphocytes (using PI negative, FSC-W/H low, SSC-W/H low, FSC/SSC-A). 2). Selection of CD8 positive and "dump" (CD4, 14, 16, 19, 40) negative cells. 3). Selection of CD8$^+$ T cells that are positive in two MHC multimer channels, and negative in the six other MHC multimer channels.

Enrichment of Antigen-Specific T Cells

Antigen-specific T cells were stained with PE-multimers (1.25 µL of a 100 µg/mL stock of each individual PE-multimer for $10^7$ PBMCs) for 1 hr at 4° C. Subsequently, cells were washed, and incubated with 20 µL anti-PE Abs coated magnetic beads (Miltenyi). Cells were then isolated by MACS (Miltenyi), using an LS column and following the manufacturer's protocol. Eluted cells were washed and resuspended in 200 µL T cell medium (IMDM (Gibco) with 10% human serum (Invitrogen), 100 IU/mL IL-2 (Proleukin) and 20 ng/mL IL-15 (Peprotech) with 5000 anti-CD3/CD28 Dynabeads (Invitrogen). Enriched cells were cultured in 96-well plates and resuspended the next day. Cultures were split and refreshed with medium a least twice a week. After 2-3 weeks, antigen-specific T cell responses were measured by combinatorial coding based MHC multimer flow cytometry.

T Cell Sorting and Cultures

T cells were stained with the relevant pMHC multimer and then sorted on a MoFlo (Dako) or FACSAria (Becton Dickinson) into $10^5$ irradiated feeder cells (JY plus allogeneic PBMCs). Cells were spun and resuspended in IMDM with 10% human serum, 100 IU/mL IL-2 and 0.5 µg/mL PHA (Biochrom AG). Cultures were restimulated every second week. Established cultures were tested for antigen-specificity by MHC multimer staining.

Cytokine Release Assay

T2-A3 cells were loaded with the indicated peptides for 1 hour and washed once. $1 \times 10^5$ T cells from indicated cultures were then incubated with $1 \times 10^5$ of T2-A3 cells for 4 h at 37° C. in IMDM with 10% human serum and protein transport inhibitor (BD GolgiPlug). Cells were stained with PE conjugated anti-CD8 Ab (SK1, BD) for 15 min at 25° C., fixed and permeabilized (BD Cytofix/Cytoperm Kit), and stained with APC conjugated anti-IFNgamma Ab (25723.11, BD) for 30 min at 4° C. Samples were analyzed by flow cytometry (Cyan, Dako), data analysis was performed using FlowJo.

Example 1

With the aim to develop a combinatorial encoding scheme that is based on the assembly of defined codes on target cells of interest, firstly, the feasibility was determined of using a set of 6 different quantum dots (Qdots, characteristics listed in FIG. 2) for the detection of antigen-specific T cell responses.

Quantum dots are fluorescent nanocrystals with a distinct emission wavelength based on their diameter and composition that exhibit very narrow emission spectra (REF), making them well-suited for experiments in which large numbers of fluorochromes are used simultaneously.

By analysis of peripheral blood CMV-specific CD8$^+$ T cell responses, it was established that MHC complexes that were multimerized by coupling to streptavidin-conjugated Qdots or standard allophycocyanin (APC) or phycoerythrin (PE) could all be utilized to detect antigen-specific T cell populations (data not shown).

Subsequently, it was tested whether antigen-specific T cell populations could also reliably be identified by the binding two MHC multimers that contain the same antigenic peptide, but that are coupled to a different fluorochrome. Testing of pMHC class I complexes conjugated to all 28 possible combinations of two different fluorochromes demonstrated that such dual encoding can in all cases identify the appropriate T cell population.

The simultaneous staining of T cells with two differentially labeled MHC multimers that contain the same antigenic peptide leads to a small reduction in fluorescence intensity for each channel (a factor of 2 at equimolarity), due to competition for binding to the limited set of available TCRs on the T cell surface. To limit a negative effect of competition on the ability to visualize antigen-specific T cell populations, the three qDots that gave the lowest intensity signal in the flow cytometric system (Q565, Q585 and Q800) were used in a 2:1 ratio rather than 1:1 ratio relative to the other fluorochromes, and the combinations Q565+Q585, Q565+Q800 and Q585+Q800—for which an adjustment in the ratio is evidently not practical—were not used in subsequent experiments.

The present example shows that differently labeled antigen presenting compounds loaded with the same antigen are capable of binding to antigen responsive cells, thereby, through detection of these different labels, allowing detection of these cells in a sample.

Example 2

Antigen-specific T cells populations can be present at very low frequencies and MHC multimers do show background staining in flow cytometry. To test whether the detection of antigen-specific T cells through the use of combinatorial codes affects background levels, or the frequency of antigen-specific T cells detected, PBMCs containing HLA-A2 CMV$_{NLV}$ specific T cells were stained with control multimers or with HLA-A2 CMV$_{NLV}$ multimers and were analyzed by flow cytometry.

Specifically, PBMCs were either incubated with the 8 different single-encoded MHC multimers in 8 separate stainings, or with the 25 dual-encoded MHC multimers in 25 separate stainings. T cells were considered positive when staining above background either in one channel (in case of single color stainings) or when staining positive in both the relevant channels (in case of dual color stainings).

Figure 3:
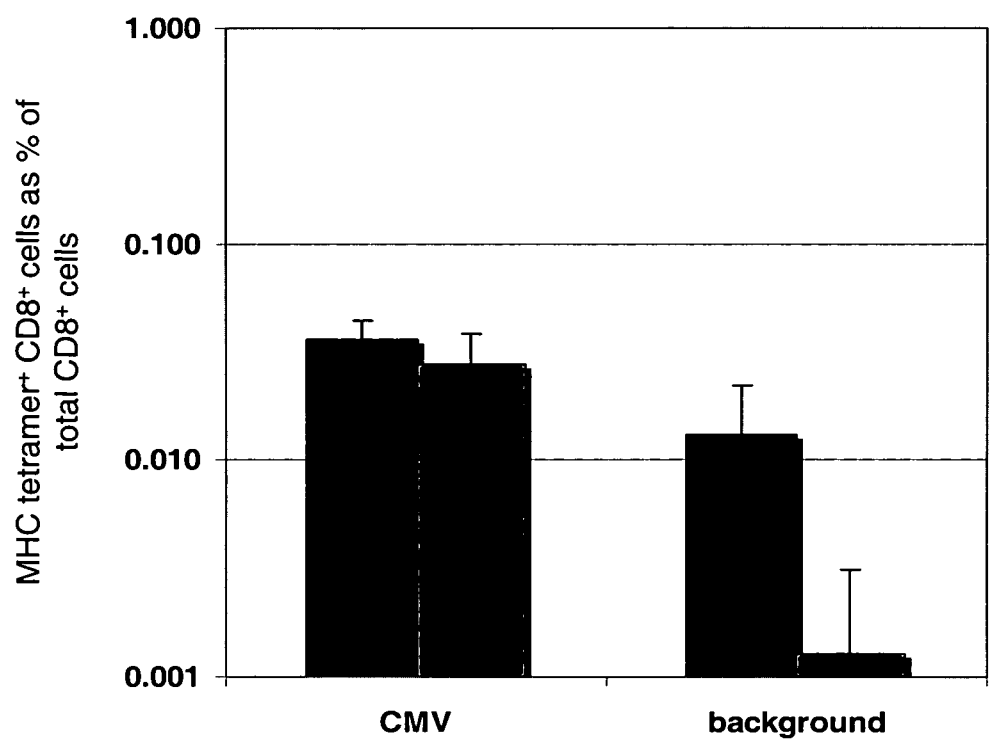
FIG. 3: shows the reduction of background signal by use of dual color-encoded pMHC multimers. Grey bars: PBMCs stained with 25 different dual color encoded combinations of MHC multimers containing either the $CMV_{NLV}$ epitope ('CMV') or the control p* peptide (Background). Black bars: PBMCs stained with the 8 different single color-encoded MHC multimers (PE, APC, Q565, Q585, Q605, Q655, Q705 and Q800) containing either the $CMV_{NLV}$ epitope ('CMV') or the control p* peptide ('Background')

As can be seen in FIG. 3, the frequency of (false-positive) cells in the background samples is approximately 10-fold lower when using a dual encoding scheme as compared to the traditional single staining approach, showing that dual color encoding of MHC multimers is a powerful tool to reduce background signals.

Example 3

Figure 4:
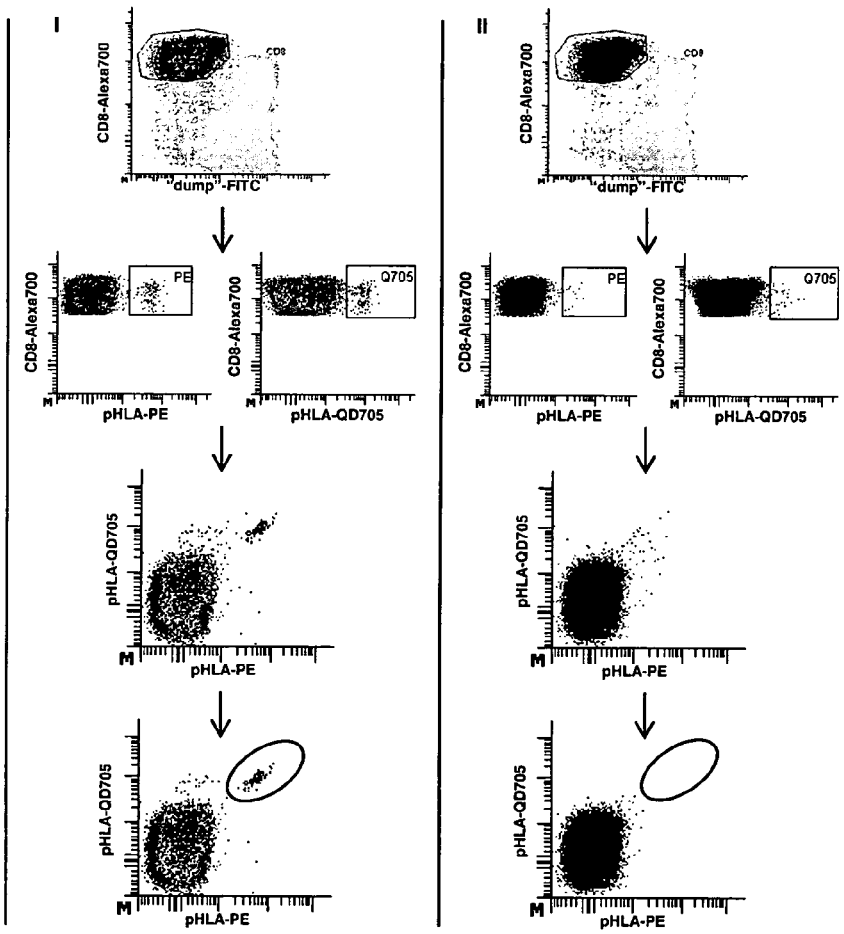
FIG. 4: shows an schematic overview of the gating strategy used for identification of pMHC specific T cells after staining with dual color-encoded pMHC multimers.

Having established the feasibility of dual color encoding, it was then examined whether multiple dual color-encoded pMHC multimer stainings can be performed in parallel on a single sample. In order to analyze T cells reactive with any of the dual color-encoded pMHC multimers in a single sample, a gating strategy was first developed (FIG. 4).

In brief, single live cells were selected based on forward and sideward scatter, cell width/height and negative propidium iodide staining. From this pool, cells that stained positive for CD8 and negative for CD4, CD14, CD16, CD19 and CD40 ("dump"-channel, van Oijen et al., 2004) were further identified as relevant CD8$^+$ T cells. To the analyzed T cell populations reactive with any of the dual color-encoded pMHC multimers, gates were generated based on each of the 8 individual fluorochromes used for MHC multimer generation.

This strategy, that identifies T cells that show signal above background in a given combination of two channels, and that are negative in the remaining 6 channels allows the simultaneous analysis of 25 different combinations in one flow cytometry experiment while at the same time reducing background staining.

Example 4

To test the potential value of the combinatorial coding technique in the large scale analysis of T cell responses, a panel of 25 different MHC multimers was generated containing a range of known viral and cancer-associated epitopes for the human MHC alleles HLA-A1, -A2, -A3 and -B7 (Table 1) by MHC peptide exchange (Toebes et al., 2006; Rodenko et al., 2006; Bakker et al., 2008). Each of these pMHC multimers was subsequently coupled to two fluorochromes generating the set of unique codes described in Table 1.

To be able to compare the data obtained by combinatorial coding with conventional MHC-multimer analysis, the set of 25 different pMHC multimers was also coupled to PE. In addition, in order to determine the background of combinatorial encoding, a set of irrelevant pMHC multimers in all two color combinations was also prepared. Subsequently, PBMCs from 3 healthy donors covering all 4 HLA alleles were then analyzed by 1) one single staining with the collection of dual color encoded viral and cancer epitope containing pMHC multimers, 2). One single staining with a mix of dual color encoded irrelevant pMHC multimers, 3). 25 separate stainings with all 25 PE-labeled pMHC multimers, or 4). 25 separate stainings with all individual dual color encoded pMHC multimers.

The comparison of '1' and '4' is of particular interest as it reveals whether the simultaneous presence of a large number of unrelated pMHC multimers that are labeled with the same fluorochromes, or the presence of high pMHC concentrations influences background signals.

Figure 5:
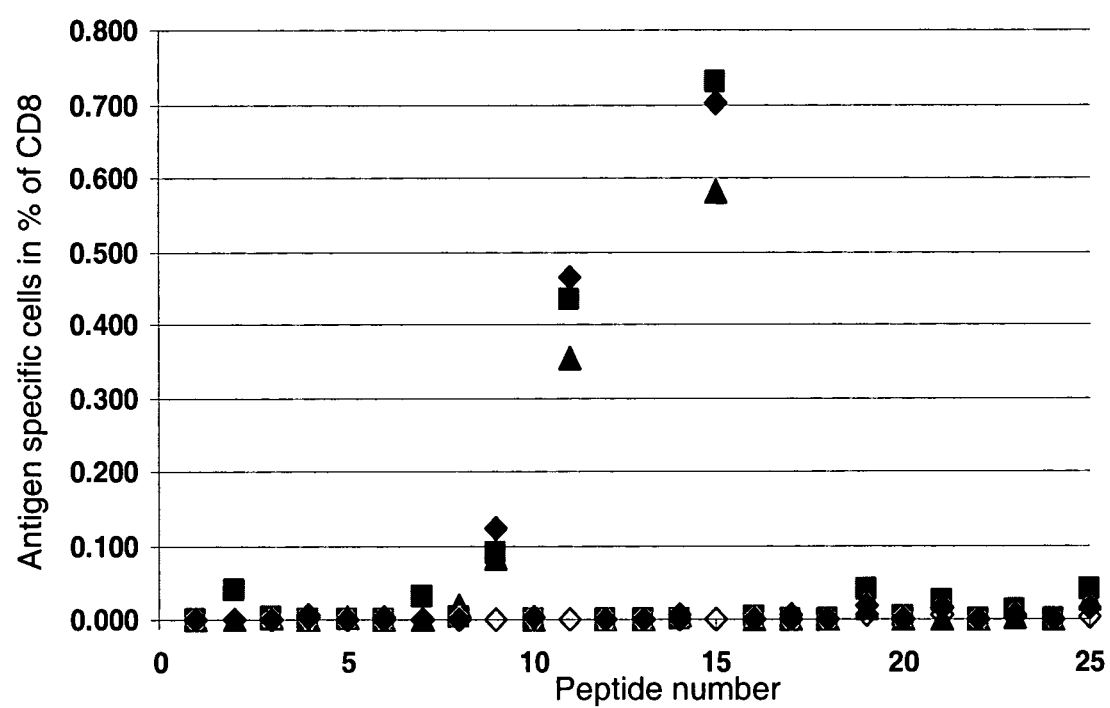
FIG. 5: shows multiplex detection of virus-specific T cell responses through combinatorial coding. Virus specific T cell responses were analyzed in PBMC of one healthy donor: I) by staining one sample with a mix of 25 different pMHC multimers each encoded by a dual color code; II) by staining 25 individual samples with pMHC multimers containing one of the 25 peptides coupled to a specific dual color code; III) by staining 25 individual samples with classical PE-labelled MHC multimers containing one of the peptides; and IV) by staining one sample with a mix of irrelevant pMHC multimers each encoded by a dual color code. I-IV: dot plots of antigen-specific T cell populations detected at a frequency >0.03% in 'I. V: Graphical representation of the frequency of antigen-specific CD8+ T cells directed against the 25 epitopes used (Suppl. Table 1), as detected by PE-labelled MHC multimer staining (▩) by dual color-encoded MHC multimers with 25 specificities per sample (♦); by dual color-encoded MHC multimers with one pMHC specificity per sample (▲); by dual color-encoded MHC multimers loaded with a control peptide (◇).
Figure 6:
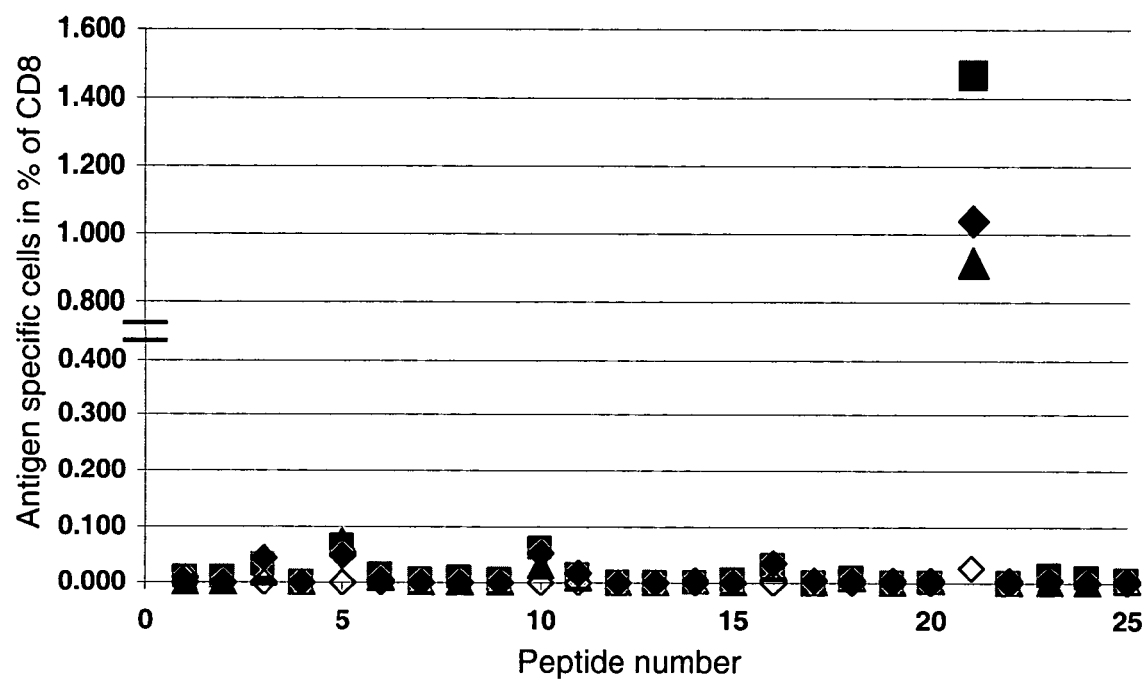
FIG. 6: shows multiplex detection of virus-specific T cell responses through combinatorial coding. Virus specific T cell responses were analyzed in PBMC of one healthy donor: I) by staining one sample with a mix of 25 different pMHC multimers each encoded by a dual color code; II) by staining 25 individual samples with pMHC multimers containing one of the 25 peptides coupled to a specific dual color code; III) by staining 25 individual samples with classical PE-labelled MHC multimers containing one of the peptides; and IV) by staining one sample with a mix of irrelevant pMHC multimers each encoded by a dual color code. I-IV: dot plots of antigen-specific T cell populations detected at a frequency >0.03% in 'I. V: Graphical representation of the frequency of antigen-specific CD8+ T cells directed against the 25 epitopes used (Suppl. Table 1), as detected by PE-labelled MHC multimer staining (▩) by dual color-encoded MHC multimers with 25 specificities per sample (♦); by dual color-encoded MHC multimers with one pMHC specificity per sample (▲); by dual color-encoded MHC multimers loaded with a control peptide (◇).
Figure 7:
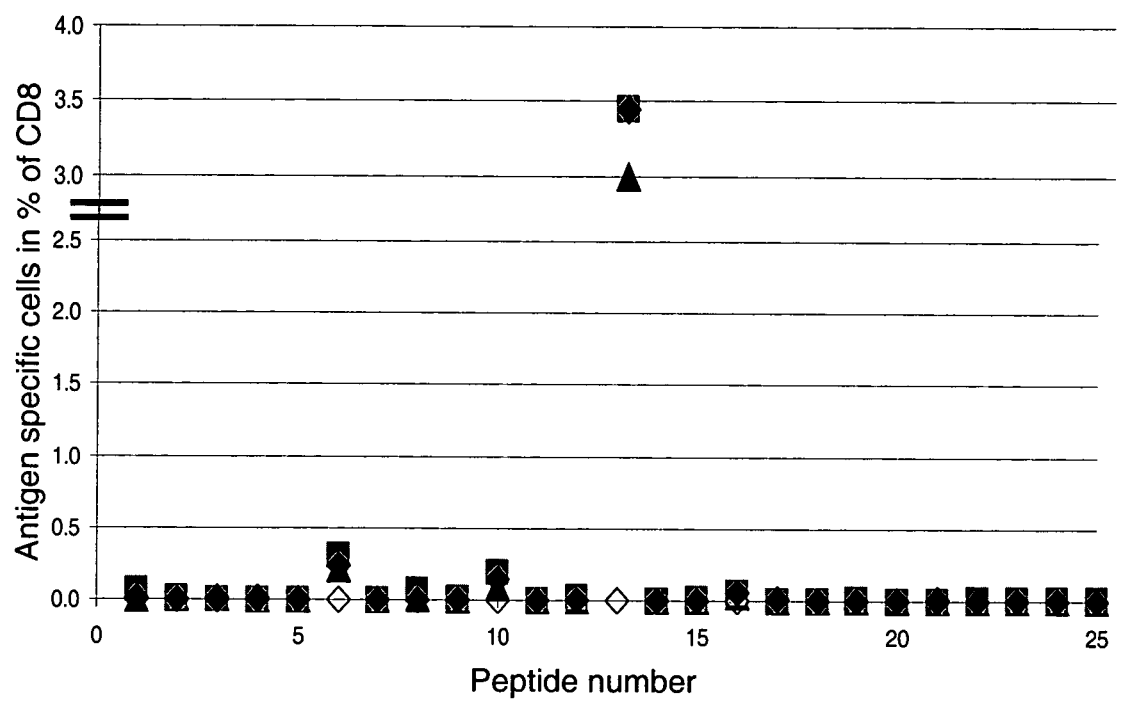
FIG. 7: shows multiplex detection of virus-specific T cell responses through combinatorial coding. Virus specific T cell responses were analyzed in PBMC of one healthy donor: I) by staining one sample with a mix of 25 different pMHC multimers each encoded by a dual color code; II) by staining 25 individual samples with pMHC multimers containing one of the 25 peptides coupled to a specific dual color code; III) by staining 25 individual samples with classical PE-labelled MHC multimers containing one of the peptides; and IV) by staining one sample with a mix of irrelevant pMHC multimers each encoded by a dual color code. I-IV: dot plots of antigen-specific T cell populations detected at a frequency >0.03% in 'I. V: Graphical representation of the frequency of antigen-specific CD8+ T cells directed against the 25 epitopes used (Suppl. Table 1), as detected by PE-labelled MHC multimer staining (■) by dual color-encoded MHC multimers with 25 specificities per sample (♦); by dual color-encoded MHC multimers with one pMHC specificity per sample (▲); by dual color-encoded MHC multimers loaded with a control peptide (◇).

The experiment was performed in a blinded fashion, both with respect to the HLA haplotype of the donors and with respect to prior analysis of antigen-specific T cell responses in these donors. Analysis of disease/pathogen-specific T cell responses in the 3 donors with these approaches revealed that combinatorial encoding of pMHC multimers allows for the visualization of a number of antigen-specific T cell populations in one single sample (FIGS. 5-7)

Figure 8:
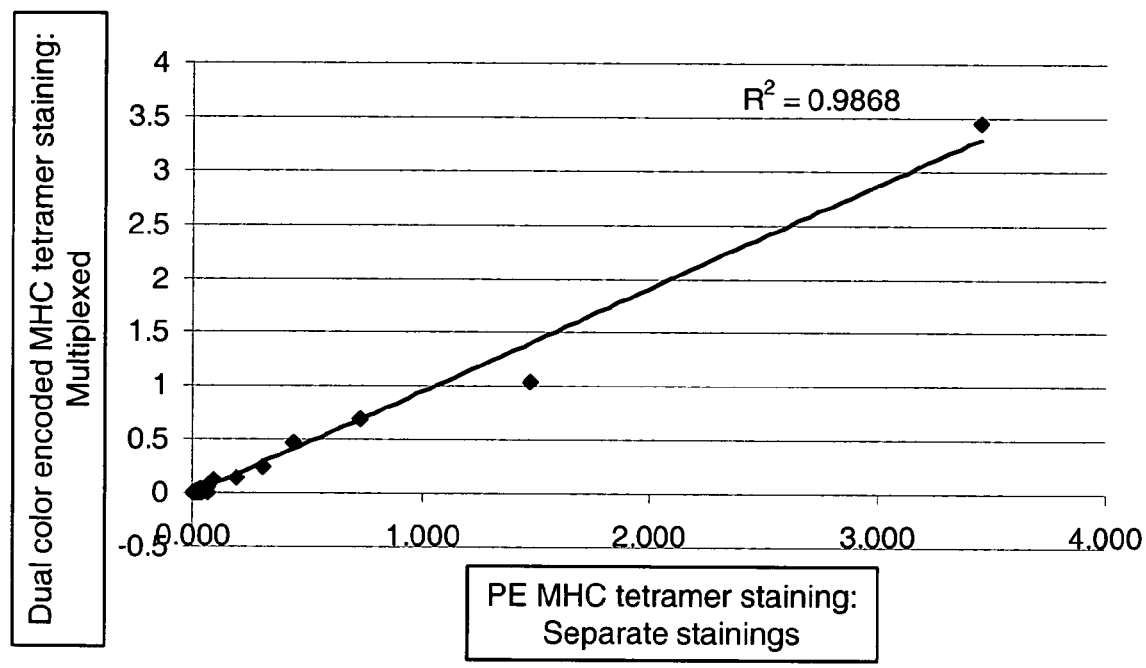
FIG. 8: shows the correlation between different T cell staining approaches. Correlation between antigen-specific T cell frequencies as detected by classical PE-labelled MHC multimer staining (X-axis) and by dual color-encoded MHC multimer staining with 25 specificities per sample (Y-axis).

Importantly, the Same Virus-Specific T Cell populations were found in each donor when analyzed by a large series of individual PE-multimer stainings. Furthermore, a direct comparison of the separate PE-coupled MHC multimer stainings with the multiplex staining using the collection of 25 dual-coded MHC multimers reveals a very high correlation between the two approaches for visualizing antigen-specific T cell populations, both when examining high frequency and low frequency T cell populations (FIG. 8).

Figure 9:
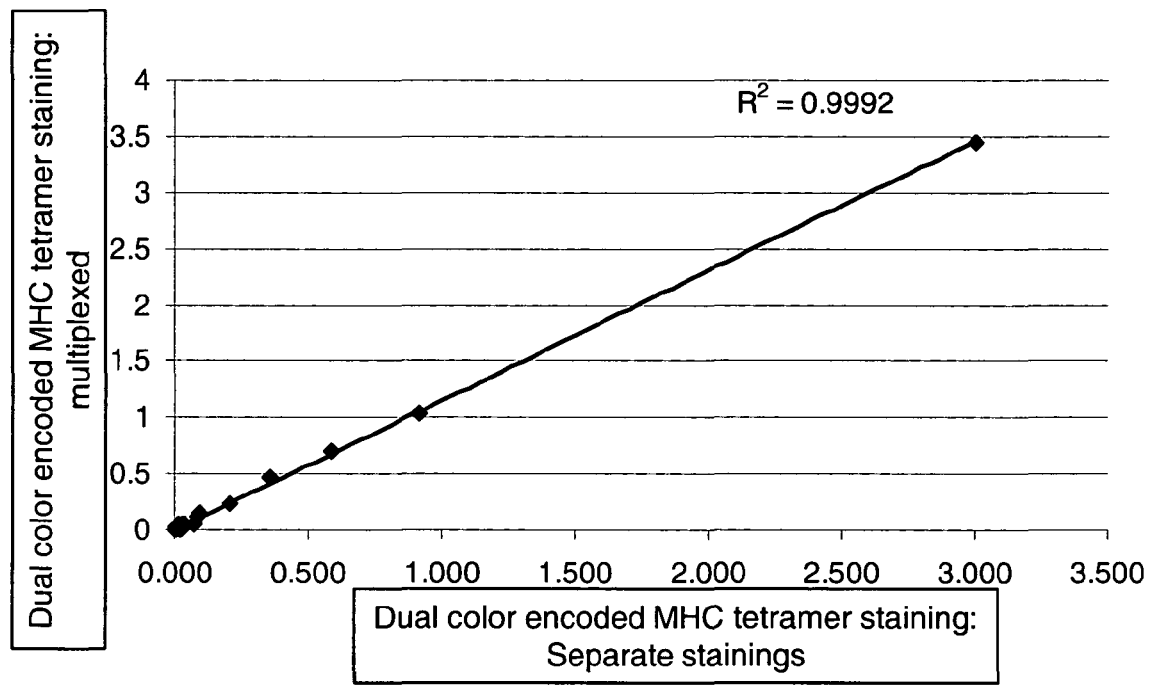
FIG. 9: shows the correlation between different T cell staining approaches. Correlation between antigen-specific T cell frequencies as detected by dual color-encoded MHC multimers with one pMHC specificity per sample (X-axis) and by dual color-encoded MHC multimer staining with 25 specificities per sample (Y-axis).

Furthermore, comparison of the data obtained upon analysis of PBMCs stained with the collection of dual color-encoded pMHC multimers in one sample versus the same set of dual color-encoded pMHC multimers used in 25 separate stainings also reveals a very high correlation (FIG. 9).

This latter finding indicates that the simultaneous measurement of multiple antigen specificities by incubation with sets of MHC multimers in which each pMHC multimer is coupled to a distinct combination of fluorochromes is feasible, even though the same fluorochrome is coupled to a large number of MHC complexes containing different peptides.

Thus, potential cross-reactivity of T cells with any of the many irrelevant pMHC complexes in the staining mix is shown not to be an issue. Furthermore, these observations indicate that using a mixture containing a high concentration of multimeric MHC molecules does not interfere with MHC multimer staining. Finally, comparison of the signals observed when using the dual color-encoded pMHC set occupied with disease/pathogen-associated epitopes with the signal observed when using the collection of 25 irrelevant MHC multimers indicates that the sensitivity of the approach is high, and T cell populations as infrequent as 0.03% of CD8 positive cells can be identified (FIGS. 5-7).

Example 5

As the experiments above demonstrated that the envisioned combinatorial coding approach can be utilized to visualize a multitude of T cell populations in a single sample, its potential value in epitope identification was evaluated.

In a recent screen set up to identify potential HLA-A3 associated melanoma epitopes 22 peptides were identified from 4 different melanoma associated proteins that displayed a high binding affinity for HLA-A3. This set included all 4 previously described HLA-A3 associated epitopes as well as 18 potential novel epitopes.

To address the feasibility of screening small patient samples for responses against the set of (potential) epitopes, MHC reagents were generated by peptide-exchange for all 22 epitopes, as well as for 3 HLA-A3-associated EBV- and influenza A-derived epitopes. To be able to also reveal low-level T cell responses, a single MACS-based enrichment step with 22 pMHC multimers containing the possible tumor-associated epitopes was performed, followed by short term in vitro expansion of the enriched cells.

The 25 different pMHC multimers were then coupled to two fluorochromes in a 2-dimensional combinatorial coding scheme and used to screen the enriched PBMCs from 27 HLA-A3 positive melanoma patients.

Using this approach of parallel MHC multimer staining, the presence could be confirmed of T cell responses directed against 3 previously described gp100-associated epitopes. Furthermore, CD8$^+$ T cell responses were observed against a previously unknown epitope derived from human gp100 (QLRALDGGNK-SEQ ID NO: 1), against 2 previously unknown epitopes derived from Nodal (SLYRDPLPR-SEQ ID NO: 2 and HAYIQSLLK SEQ ID NO: 3), and against 1 previously unknown epitope derived from Tyrp2 (RMYNM-VPFF-SEQ ID NO: 4) (Table 2).

Figure 10:
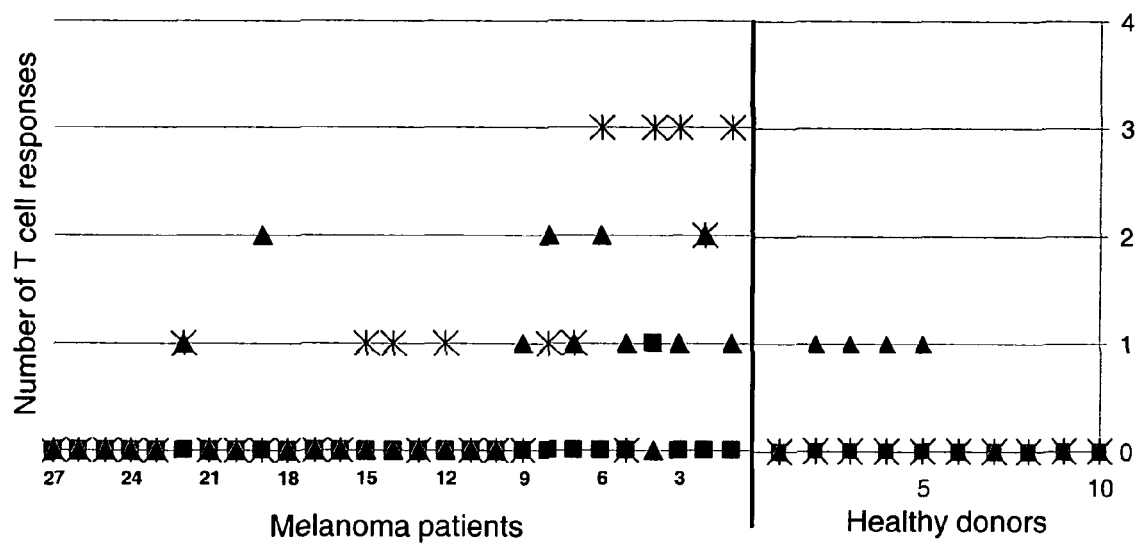
FIG. 10: shows T cell responses against Melanoma-associated peptides. Summary of antigen-specific T cell responses detected in melanoma patients and healthy donors, directed against: HLA-A3-restricted virus-derived T cell epitopes ($EBV_{RLR}$, $EBV_{RVR}$, $FLU_{ILR}$), direct ex-vivo detection (▲); 22 melanoma restricted peptides, direct ex-vivo detection (▩); or 22 melanoma restricted peptides, after T cell enrichment and in vitro expansion (*).

Importantly, when PBMC from 10 healthy HLA-A3+ donors were analyzed in the same manner, no responses were observed in any of the donors, whereas T cell responses against viral epitopes were equally abundant in both groups (FIG. 10).

In order to determine whether the observed T cell populations show functional activity against target cells that display the corresponding peptides antigen-specific T cells were sorted from PBMCs from the different patients and expanded in vitro. The resulting T cell populations were then tested for antigen specificity with an intercellular cytokine assay after incubation with peptide loaded target cells (FIG. 11).

Figure 11:
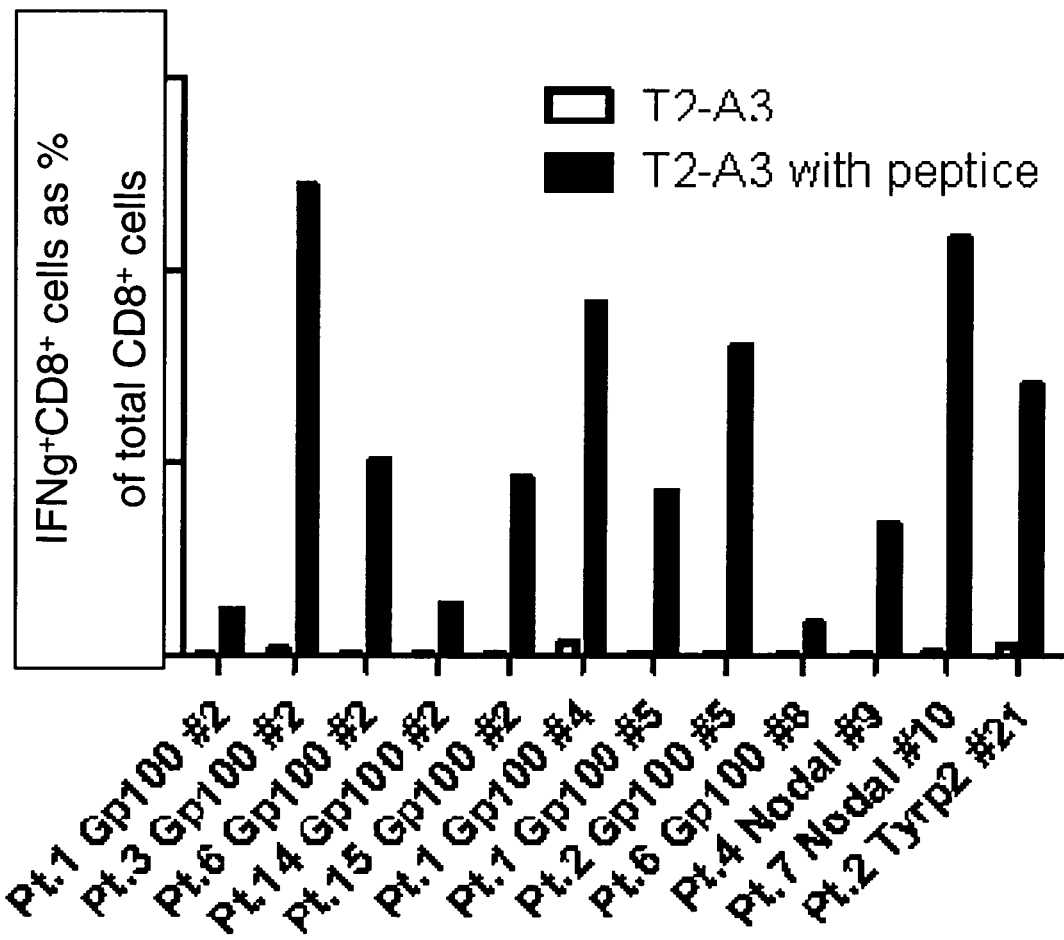
FIG. 11: shows Intracellular IFNγ staining confirming the peptide specificity of MHC multimer-reactive T cell populations defined by combinatorial coding. Peptide numbers refer to the sequences in Table 2.

All cultures displayed IFNgamma production when incubated with their cognate antigen (FIG. 11). No response was observed when the T cell cultures were incubated with cells that were not loaded with peptide.

These results show that a previously described list of peptides that have a high binding-affinity for HLA-A3 contains at least 8 melanoma-associated epitopes against which T cell responses can be observed in melanoma patients of which 5 have not been described previously. Furthermore, the screens that were performed on the available patient material would not have been feasible without the possibility of multiplex analysis offered by the multicolor-encoding of antigen specificities according to the present invention.

CONCLUSION

The combinatorial coding technique according to the present invention is demonstrated to be a valuable tool for the detection and analysis of multiple immune responses simultaneously.

A combinatorial coding strategy was developed that allows the parallel detection of a multitude of different T cell populations within a single sample. Detection of antigen-specific T cells from peripheral blood by combinatorial coding is as efficient as detection with conventional PE labeled multimers, but results in a significantly increased sensitivity, and most importantly, allows comprehensive screens to be performed on patient material.

The feasibility of large-scale screening of patient material was demonstrated by analyzing T cell responses against known and potential melanoma associated antigens in peripheral blood from melanoma patients. These screens confirmed the existence of T cell responses against known T cell epitopes and led to the identification of a number of novel melanoma-associated T cell responses in the context of HLA-A3.

It is concluded that combinatorial coding of peptide-MHC conjugates allows the high-throughput analysis of antigen-specific T cell immunity in a single sample.

TABLE 1

List of 25 virus and cancer derived T cell epitopes. For each epitope MHC multimers were encoded by the indicated fluorochrome combination.

| No. | Peptide | Coding |
|---|---|---|
| 1 | A2 HPV E6 | PE & APC |
| 2 | A3 CMV pp150 TTV | PE & Q565 |
| 3 | A2 FLU GIL | PE & Q585 |
| 4 | A2 gp100 2M | PE & Q605 |
| 5 | A2 EBV LMP2 CLG | PE & Q655 |
| 6 | A2 EBV BMF1 GLC | PE & Q705 |
| 7 | A2 Tyrosinase | PE & Q800 |
| 8 | A2 Sur1m2 | APC & Q565 |
| 9 | A1 CMV pp65 YSE | APC & Q585 |
| 10 | A2 EBV LMP2 FLY | APC & Q605 |
| 11 | A3 FLU NP ILR | APC & Q655 |
| 12 | A2 HA-2 | APC & Q705 |
| 13 | A2 CMV pp65 NLV | APC & Q800 |
| 14 | B7 CMV pp65 TPR | Q565 & Q585 |
| | | Q565 & Q605 |
| 15 | A1 CMV pp50 VTE | Q565 & Q655 |
| 16 | A2 EBV BRLF1 YVL | Q565 & Q705 |
| | | Q565 & Q800 |
| 17 | A2 HPV E7 | Q585 & Q605 |
| 18 | A3 EBV EBNA 3a RLR | Q585 & Q655 |
| 19 | A1 FLU BP-VSD | Q585 & Q705 |
| | | Q585 & Q800 |
| 20 | B7 CMV pp65 RPH-L | Q605 & Q655 |
| 21 | B7 EBV EBNA RPP | Q605 & Q705 |
| 22 | A2 HY | Q605 & Q800 |
| 23 | A3 CMV pp150 TVY | Q655 & Q705 |
| 24 | A2 CMV IE1 VLE | Q655 & Q800 |
| 25 | A3 EBV BRLF1 RVR | Q705 & Q800 |

TABLE 2

List of the 22 melanoma-associated HLA-A3 ligands and three virus derived HLA-A3 restricted epitopes. For each peptide MHC multimers were encoded by the indicated fluorochrome combination.

| No | Protein | Peptide | Position | Coding |
|---|---|---|---|---|
| 1 | Gp100 | IALNFPGSQK (SEQ ID NO: 6) | 86-95 | PE & APC |
| 2 | | LIYRRRLMK (SEQ ID NO: 7) | 614-622 | PE & Q565 |
| 3 | | GTATLRLVK (SEQ ID NO: 8) | 460-468 | PE & Q585 |
| 4 | | ALLAVGATK (SEQ ID NO: 9) | 17-25 | PE & Q605 |
| 5 | | ALNFPGSQK (SEQ ID NO: 10) | 87-95 | PE & Q655 |
| 6 | | GVSRQLRTK (SEQ ID NO: 11) | 34-42 | PE & Q705 |
| 7 | | QLVLHQILK (SEQ ID NO: 12) | 551-559 | PE & Q800 |
| 8 | | QLRALDGGNK (SEQ ID NO: 1) | 221-230 | APC & Q565 |
| 9 | Nodal | SLYRDPLPR (SEQ ID NO: 2) | 46-54 | APC & Q585 |
| 10 | | HAYIQSLLK (SEQ ID NO: 3) | 293-301 | APC & Q605 |
| 11 | | KTKPLSMLY (SEQ ID NO: 13) | 317-325 | APC & Q655 |

TABLE 2-continued

List of the 22 melanoma-associated HLA-A3 ligands and three virus derived HLA-A3 restricted epitopes. For each peptide MHC multimers were encoded by the indicated fluorochrome combination.

| No | Protein | Peptide | Position | Coding |
|---|---|---|---|---|
| 12 |  | RVAGECWPR (SEQ ID NO: 14) | 175-183 | APC & Q705 |
| 13 | Tyr | YMVPFIPLYR (SEQ ID NO: 15) | 425-434 | APC & Q800 |
| 14 |  | SLLCRHKRK (SEQ ID NO: 16) | 497-505 | Q565 & Q605 |
| 15 |  | VSSKNLMEK (SEQ ID NO: 17) | 25-33 | Q565 & Q655 |
| 16 |  | GLVSLLCRHK (SEQ ID NO: 18) | 494-503 | Q565 & Q705 |
| 17 | Tyrp1 | SLPYWNFATR (SEQ ID NO: 19) | 245-254 | Q585 & Q605 |
| 18 |  | ASYLIRARR (SEQ ID NO: 20) | 497-505 | Q585 & Q655 |
| 19 | Tyrp2 | TLLGPGRPYR (SEQ ID NO: 21) | 196-205 | Q585 & Q705 |
| 20 |  | GTYEGLLRR (SEQ ID NO: 5) | 301-309 | Q605 & Q655 |
| 21 |  | RMYNMVPFF (SEQ ID NO: 4) | 461-469 | Q605 & Q705 |
| 22 |  | VLLAFLQYR (SEQ ID NO: 22) | 521-529 | Q605 & Q800 |
| 23 | Influenza NP | ILRGSVAHK (SEQ ID NO: 23) | 265-273 | Q655 & Q705 |
| 24 | EBV EBNA 3a | RLRAEAQVK (SEQ ID NO: 24) | 603-611 | Q655 & Q800 |
| 25 | EBV BRLF1 | RVRAYTYSK (SEQ ID NO: 25) | 148-156 | Q705 & Q800 |

REFERENCES

Arstila T P, Casrouge A, Baron V, Even J, Kanellopoulos J, Kourilsky P. A direct estimate of the human alphabeta T cell receptor diversity. Science 1999; 286(5441):958-61.

Altman J D, Moss P A, Goulder P J, Barouch D H, McHeyzer-Williams M G, Bell J I, et al. Phenotypic analysis of antigen-specific T lymphocytes. Science 1996; 274(5284):94-6.

Chattopadhyay P K, Price D A, Harper T F, Betts M R, Yu J, Gostick E, et al. Quantum dot semiconductor nanocrystals for immunophenotyping by polychromatic flow cytometry. Nat Med 2006; 12(8):972-7.

Soen Y, Chen D S, Kraft D L, Davis M M, Brown P O. Detection and characterization of cellular immune responses using peptide-MHC microarrays. PLoS Biol 2003; 1(3):E65.

Stone J D, Demkowicz W E, Jr., Stern L J. HLA-restricted epitope identification and detection of functional T cell responses by using MHC-peptide and costimulatory microarrays. Proc Natl Acad Sci USA 2005; 102(10):3744-9.

Xu H, Sha M Y, Wong E Y, Uphoff J, Xu Y, Treadway J A, et al. Multiplexed SNP genotyping using the Qbead system: a quantum dot-encoded microsphere-based assay. Nucleic Acids Res 2003; 31(8):e43.

Haanen J B, Wolkers M C, Kruisbeek A M, Schumacher T N. Selective expansion of cross-reactive CD8(+) memory T cells by viral variants. J Exp Med 1999; 190(9):1319-28.

van Oijen M, Bins A, Elias S, Sein J, Weder P, de Gast G, et al. On the role of melanoma-specific CD8+ T-cell immunity in disease progression of advanced-stage melanoma patients. Clin Cancer Res 2004; 10(14):4754-60.

Toebes M, Coccoris M, Bins A, Rodenko B, Gomez R, Nieuwkoop N J, et al. Design and use of conditional MHC class I ligands. Nat Med 2006; 12(2):246-51.

Rodenko B, Toebes M, Hadrup S R, van Esch W J, Molenaar A M, Schumacher T N, et al. Generation of peptide-MHC class I complexes through UV-mediated ligand exchange. Nat Protoc 2006; 1(3):1120-32.

Bakker A H, Hoppes R, Linnemann C, Toebes M, Rodenko B, Berkers C R, et al. Conditional MHC class I ligands and peptide exchange technology for the human MHC gene products HLA-A1, -A3, -A11, and -B7. Proc Natl Acad Sci USA 2008; 105(10):3825-30.

Garboczi D N, Hung D T, Wiley D C. HLA-A2-peptide complexes: refolding and crystallization of molecules expressed in *Escherichia coli* and complexed with single antigenic peptides. Proc Natl Acad Sci USA 1992; 89(8):3429-33.

The invention claimed is:

1. A method for detecting antigen responsive cells in a sample comprising:
   providing antigen-containing antigen presenting compounds, each antigen-containing antigen presenting compound carrying at least one label, with two or more predetermined antigens, wherein each antigen is represented by at least two different labels;
   contacting said antigen-containing antigen presenting compounds with said sample;
   detecting binding of said antigen-containing antigen presenting compounds to said antigen responsive cells, thereby detecting cells responsive to at least one of said antigens; wherein the presence of the at least one of said antigens is detected by detecting a signal emitted by the at least two different labels bound to an antigen responsive cell through said antigen presenting compounds loaded with the at least one of said antigens.

2. The method according to claim 1, wherein said two or more predetermined antigens are selected from the group consisting of three or more, four or more, five or more, six or more, seven or more, eight or more, ten or more, eleven or more, twelve or more, thirteen or more, fourteen or more, fifteen or more, sixteen or more, seventeen or more, eighteen or more, nineteen or more, twenty or more, twenty or more, twenty-one or more, twenty-two or more, twenty-three or more, twenty-four or more, twenty-five or more, twenty-six or more, twenty-seven or more, and twenty-eight or more.

3. The method according to claim 1, wherein said antigen-containing antigen presenting compounds are provided with one label and at least one of said antigens is represented by at least two differently labelled antigen-containing antigen presenting compounds.

4. The method according to claim 1, wherein said antigen-containing antigen presenting compounds are provided with at least two different labels and at least one of said antigens is represented by one labelled antigen-containing antigen presenting compound.

5. The method according to claim 1, wherein at least one of said antigens is a peptide.

6. The method according to claim 1, wherein said antigen-containing antigen presenting compounds are major histocompatibility complexes (MHC).

7. The method according to claim 6, wherein said major histocompatibility complexes (MHC) are multimeric major histocompatibility complexes (MHC).

8. The method according to claim 1, wherein said antigen responsive cells are T-cells and/or B-cells.

9. The method according to claim 1, wherein said labels are fluorescent labels.

10. The method according to claim 9, wherein said fluorescent labels comprise qDots.

11. The method according to claim 1, wherein the number of different labels is selected from the group consisting three or more, four or more, five or more, six or more, seven or more, and eight or more.

12. The method according to claim 1, wherein at least one of said antigens is represented by at least three or at least four different labels.

13. The method according to claim 1, wherein said sample is a blood sample or a blood derived sample.

14. The method according to claim 1, wherein said detection comprises flow cytometry.

15. The method according to claim 1, wherein said at least two labels represent a single antigen for the detecting of antigen responsive cells in a sample.

16. The method according to claim 1, wherein at least one of said antigens comprises an epitope.

17. A method for detecting binding of a ligand to a cell or a cell-bound receptor comprising:
   labelling said ligand with at least one ligand-binding compound, the ligand-binding compound having at least one label, wherein the ligand is labelled with at least two different labels; and
   detecting said cell or cell-bound receptor, wherein said cell or cell-bound receptor is detected by detecting a signal emitted by the at least two different labels based on binding of the cell or cell-bound receptor to said ligand.

* * * * *

UNITED STATES PATENT AND TRADEMARK OFFICE
CERTIFICATE OF CORRECTION

PATENT NO. : 9,151,757 B2
APPLICATION NO. : 13/127136
DATED : October 6, 2015
INVENTOR(S) : Sine Reker-Hadrup et al.

It is certified that error appears in the above-identified patent and that said Letters Patent is hereby corrected as shown below:

On The Title Page, Column 2, Item (56) PUBLICATIONS, Line 2, delete "-AL," and insert
-- -A1, --

On The Title Page, Column 2, Item (57) ABSTRACT, Line 4, delete "(NHC)." and insert
-- (MHC). --

In The Claims

Column 23, Line 54, Claim 2, delete "twenty or more, twenty or more," and insert -- twenty or more, --

Signed and Sealed this
Fifteenth Day of March, 2016

Michelle K. Lee
*Director of the United States Patent and Trademark Office*